United States Patent [19]

Moloney et al.

[11] Patent Number: 5,463,174

[45] Date of Patent: * Oct. 31, 1995

[54] TRANSFORMATION AND FOREIGN GENE EXPRESSION IN BRASSICA SPECIES

[75] Inventors: Maurice M. Moloney, Calgary, Canada; Sharon Radke, Davis, Calif.

[73] Assignee: Calgene Inc., Davis, Calif.

[*] Notice: The portion of the term of this patent subsequent to Feb. 23, 2010, has been disclaimed.

[21] Appl. No.: 943,815

[22] Filed: Sep. 11, 1992

Related U.S. Application Data

[63] Continuation of Ser. No. 395,131, Aug. 14, 1989, Pat. No. 5,188,958, which is a continuation of Ser. No. 54,187, May 26, 1987, abandoned, which is a continuation-in-part of Ser. No. 868,640, Mar. 29, 1986, abandoned.

[51] Int. Cl.$^6$ .............................. A01H 1/04; C12N 5/00; C12N 15/00; C12P 21/04
[52] U.S. Cl. ........................ 800/205; 800/DIG. 15; 800/DIG. 17; 435/69.1; 435/70.1; 435/172.3; 435/240.4; 435/240.5; 435/240.54
[58] Field of Search ........................... 435/69.1, 172.3, 435/240.4, 240.49, 240.5, 240.51, 240.54, 70.1; 800/205, DIG. 17, DIG. 15

[56] References Cited

U.S. PATENT DOCUMENTS

| | | | |
|---|---|---|---|
| 5,004,863 | 4/1991 | Umbeck | 800/205 |
| 5,188,958 | 2/1993 | Moloney et al. | 435/240.4 |

OTHER PUBLICATIONS

Holbrook et al. 1985. Plant Cell Reports 4:329–332.
Dieter et al. 1982. Plant Science Letters 26:233–240.
Barton et al. 1987. Plant Physiol 85:1103–1109.
Larkins et al. 1985. J. Cell. Biochem. Suppl. 9C:264.
Radke, et al., "Transformation and Regeneration of *Brassica rapa* Using *Agrobacterium tumefaciens*," Plant Cell Reports (1992) 11:499–505.
Moloney, *Crucifer Genetics Workshop III Proceedings*, (1986) pp. 35–36.
Pua et al., "Transgenic Plants of *Brassica napus* L." Bio/Technology (1987) 5:815–817.
Fry et al., "Transformation of *Brassica napus* with *Agrobacterium tumefaciens* based vectors," Plant Cell Reports (1987) 6:321–325.
Paszkowski et al., "Genetic transformation of *Brassica campestris var. rapa* protoplasts with an engineered cauliflower mosaic virus genome" Plant Mol. Bio. (1986) 6:303–312.
Charest, et al., "Strategies for *Brassica napus* Genetic Engineering," Crucifer Genetics Workshop Proceedings (1986) p. 40.
Charest, et al., "Agrobacterium-mediated transformation of thin cell layer explants from *Brassic napus* L." Theor. Appl. Genet. (1988) 75:438–445.
Ohlsson and Eriksson, "Transformation of *Brassica campestris* protoplasts with *Agrobacterium tumefaciens*," Hereditas (1988) 108:173–77.
Radke, et al., "Development of a Transformation System for *Brassica napus* Using Agrobacterium Binary Vectors," Commonwealth Agricultural Bureau & Crucifer Genetic Workshop III, Proceedings, 29th–30th May 1986, University of Guelph, Abstract No. CAB 88 1669878, p. 42.
Hiatt, et al., "Introduction and Expression In Plants of a Glyphosate Resistant aroA Gene Isolated from *Salmonella typhimurium*," Nato ASI Series A Life Sciences (1984) Jul. 4–14, 83:479–488.

(List continued on next page.)

Primary Examiner—David T. Fox

[57] ABSTRACT

Brassica species are produced by transformation of cell cultures with foreign DNA followed by regeneration of plants from transformed cells. The cells and the plants produced thereby are capable of expressing the foreign gene. The Brassica species are transformed employing a manipulated Agrobacterium transformation system, followed by regeneration of the plant tissue into plants.

29 Claims, 7 Drawing Sheets

OTHER PUBLICATIONS

Klimaszewska et al., "High Frequency Plant Regeneration from Thin Cell Layer Explants of *Brassica napus*," *Plant Cell Tissue Organ Culture* (1985) 4:183–197.

Brisson et al., "Expression of a Bacterial Gene in Plants By Using A Viral Vector," *Nature* (1984) 310(5977):511–514.

Radke et al., "Transformation of *Brassica napus* L. Using *Agrobacterium tumefaciens*: Developmentally Regulated Expression of a Reintroduced Napin Gene," *Theor. Appl. Genet.* (1988) 75:685–694.

Shahin, et al., "Transformation of cultivated tomato by a binary vector in *Agrobacterium rhizogenes*: transgenics plants with normal phenotypes harbor binary vector T–DNA, but no Ri–plasmid T–DNA," *Theor. Appl. Genet.* (1986) 72:770–777.

Brisson, et al., "Expression of a bacterial gene in plants by using a viral vector," *Nature* (1984) 310:511–514.

Radke, et al. "Transformation of *Brassica napus* L. using *Agrobacterium tumefaciens*: developmentally regulated expression of a reintroduced napin gene," *Theor. Appl. Genet.* (1988) 75:685–694.

Ondrej, "Detection of Napaline Dehydrogenase and Lysopine Dehydrogenase Activities in Crown Gall Tumors of Different Plant Species," *Biol. Plant. (1983) 5:378–384.*

Mathews, et al., "Transformation of *Brassica juncea* by *Agrobacterium tumefaciens* harboring plasmid pTiT37 and its 'rooty' mutant pTiT37.14a/a," *J. Genet.* (1986) 65:37–44.

Ooms, et al., "Genetic manipulation in cultivars of oilseed rape (*Brassica napus*) using Agrobacterium," *Theor. Appl. Genet.* (1986) 71:325–329.

Koziel, et al., "A Cauliflower Mosaic Virus Promoter Directs Expression of Kanamycin Resistance in Morphogenic Transformed Plant Cells," *J. Mol. and Appl. Genet.* (1984) 2:549–562.

Stringham, "Regeneration in Leaf–Callus Cultures of Haploid Rapeseed (*Brassica napus* L.)," *Z. Pflanzenphyiol Bd.* (1979) 92:459–562.

Dietert, et al., "Effects of Genotype on In vitro Culture in the Genus Brassica," *Science Letters* (1982) 26:233–240.

Flick, et al., "Organogenesis," *Handbook of Plant Cell Cultures*, pp. 25–26.

Dunwell, "In vitro Shoot Regeneration from Seedling Root Segments of *Brassica oleracea* and *Brasscia napus* Cultivars," *Anals of Botany* (1984) 54:341–350.

Glimelius, "High growth rate and regeneration capacity of hypocotly protoplasts in some Brassicaceae," *Physiol Plant (1984) 61:38–44.*

Mathews, et al., "Regeneration of Shoots from *Brassica juncea* (Linn) Czern and Coss Cells Transformed by *Agrobacterium tumefaciens* and Expression of Nopaline Dehydrogenase Genes," *Plant Sciences* (1985) 39:49–54.

Laser and Erickson, "Transformation of Protoplasts from *Brassica campestris* with *Agrobacterium tumefaciens*," *Physiologia Plantarum* (1985) 64:13A.

Galsky, et al., "Crown–Gall Tumors Possess Tumor-Specific Antigenic Sites on Their Cell Walls," *Plant Physiol. (1981) 67:1195–1197.*

Holbrook and Miki, "Brassica grown [sic] gall tumorigenesis and in vitro [sic] of transformed plants," *Plant Cell Reports* (1985) 4:329–332.

Bevan, et al., "Expression of tobacco mosaic virus coat protein by a cauliflower mosaic virus promoter in plants transformed by Agrobacterium," *EMBO* (1986) 4:1921–1926.

Xingcum, et al., "T–DNA Transfer and Teratome Induction of *Brassica oleracea* L," *Kexue Tongbao* (1985) 30(6):826–828.

Widholm, J. *TIBTECH* (1988) 6:265–266.

Horsch, et al., *Science* (1985) 227:1229–1231.

Fry, et al., Crucifer Genetics Workshop III, (1986) Proceedings p. 41.

Radke, et al., Crucifer Genetics Workshop (1986) Proceedings p. 42.

Moloney, *Plant Physiol.* (1984) 75(Suppl. 1)86.

Jiang, et al., *Chemical Abstracts* (1985) 103(21):175561f.

Barsby, et al. "A Rapid and Efficient Alternative Procedure for the Regeneration of Plants from Hypocotyl Protoplasts of *Brassica napus*" *Plant Cells Reports* 1986 vol. 5 101–103.

Holbrook, Larry and Charest, Pierre, Brassica Transformation via Agrobacterium tumefaciens First Canadian Plant Molecular Biology Workshop University of Guelph, Guelph, Ontario, Canada May 26–28, 1985.

TRANSFORMATION AND FOREIGN GENE EXPRESSION IN BRASSICA SPECIES

This application is a continuation of U.S. Ser. No. 07/395,131, filed Aug. 14, 1989, now U.S. Pat. No. 5,188,958, which is a file wrapper continuation of U.S. Ser. No. 07/054,187, filed May 26, 1987, now abandoned, which is a continuation-in-part of U.S. Ser. No. 06/868,640, filed Mar. 29, 1986, now abandoned.

BACKGROUND OF THE INVENTION

1. Field of the Invention

This invention is related to a method for improving genotypes and associated phenotypes in Brassica species by means of Agrobacterium-based genetic transformation.

2. Background

Cruciferous species of the tribe Brassiceae are widely used as a source of protein, oil, condiments and chemical feedstocks. Significant effort has been expended to improve the quality of cultivated Brassica species by conventional plant breeding, and a number of major successes are recorded. The methods of conventional plant breeding have been limited, however, to the movement of genes and traits from members of the genus Brassica to other of the same genus and, in a few notable examples, "wide crosses" from other closely related genera. The development of a method for introducing foreign genes into Brassica species would greatly enhance the range of traits which could be imparted to Brassica oilseeds and vegetables.

In order to obtain a reliable system for useful gene introduction into Brassica species, a number of obstacles must be overcome. These include optimization of regenerability to whole plants of the target tissue, definition of the conditions (e.g., time, bacterial concentration, and media) for the co-cultivation of the Brassica cells and Agrobacterium cells, discovery of an Agrobacterium strain of suitable virulence with Brassica for gene transfer, identification of a suitable regulatory sequence (promoter) to ensure expression of the foreign gene in the transformed tissue, and expression of a selectable marker enabling identification of transformants.

BRIEF DESCRIPTION OF RELEVANT LITERATURE

Brassica species have been widely investigated for regenerability from tissue explants. Both *Brassica napus* and *Brassica oleracea* show shoot regeneration from a variety of tissues including hypocotyls (M. F. Dietert et al., *Plant Science Letters* (1982) 26:233–240), leaf callus (G. R. Stringham, *Z. Pflanzenphysiol.* (1979) 92:459–462), roots (P. A. Lazzeri and J. M. Dunwell, *Annals of Botany* (1984) 54:341:350), and leaf and stem protoplasts (L. C. Li and H. W. Kohlenback, *Plant Cell Reports* (1982) 1:209–211; K. Glimelius, *Physiol. Plant.* (1984) 61:38–44). See also, the poster given by Radke, et al., Crucifer Genetics Workshop, Guelph, Jun. 29, 1986.

The suitability of Agrobacterium as a vector for Brassica transformation is suggested by host range studies by DeCleene and DeLey (*Botanical Rev.* (1976) 42:386–466) demonstrating several species of Brassica (including *napus, oleracea, nigra* and *campestris*) to be susceptible to Agrobacterium. Recent studies by L. A. Holbrook and B. L. Miki (*Plant Cell Reports* (1985) 4:329–332) show some evidence for the expression of characteristic Agrobacterium genes in non-regenerable tumorous tissue.

The use of *Agrobacterium tumefaciens* for transforming plants using tissue explants is described in Horsch et al. (*Science* (1985) 228:1229–1231). See also, Herrera-Estrella et al. (*Nature* (1983) 303:209–213), Fraley et al. (*Proc. Natl. Acad. Sci. USA* (1983) 80:4803–4807) and Bevan et al. (*Nature* (1983) 304:184–187). Use of the 35S promoter from cauliflower mosaic virus to direct expression of chimeric genes in plants has been reported (see C. K. Shewmaker et al., *Virology* (1985) 140:281–288 and R. C. Gardner et al., *Plant Molecular Biology* (1986) 6:221–228).

SUMMARY OF THE INVENTION

Transformed Brassica plants and tissues are provided which contain novel nucleotide constructions capable of stable expression. The transformation techniques employed are designed to optimize frequency of transformation, recovery of target tissue and regeneration of plants from the transformed tissue. Preferred techniques of the invention for obtaining the desired transformed Brassica plants include use of *Agrobacterium tumefaciens* strains (having virulence against Brassica), use of a medium during the selection process containing a less than normal carbon-source content (less than or equal to 2% sucrose or its equivalent in caloric value), use of efficient promoters, and use of hypocotyls as target tissues. The technique may make use of a feeder layer of tobacco suspension cells to assist with transformation frequency and recovery of the target tissue. Target tissue may include leaf or stem explants in addition to the hypocotyls discussed above.

BRIEF DESCRIPTION OF THE FIGURES

Lanes 1, 2, 3 and 4: *Brassica napus* cv Westar tissue transformed by A281×200 *Agrobacterium tumefaciens*.

Lanes 5 and 6: *Brassica napus* cv Westar tissue transformed by K12×200 *Agrobacterium tumefaciens*.

Lane 7: Negative control untransformed Brassica leaf tissue.

Lane 8: Bacterial neomycin phosphotransferase activity (positive control).

DESCRIPTION OF THE SPECIFIC EMBODIMENTS

Novel procedures and products are provided involving the introduction of novel nucleotide constructs into cells of *Brassica napus*, typically using leaf and hypocotyl explants, where the transformed cells of the plant express one or more genes present in the construct so as to provide at least one novel property for the plant, particularly a phenotypic property.

A number of process steps are involved in providing for efficient frequency of transformation, recovery of target tissue, and regeneration of plants from the transformed tissue. The initial stage is the selection of an *Agrobacterium tumefaciens* strain which provides for efficient transformation of Brassica. In the next stage, selection and regeneration media are employed with only a small amount of carbon-source materials (less than 2%) sucrose or its equivalent in caloric value). The construct which is used should include a transcriptional initiation region which efficiently functions in Brassica. The source of the plant cells for transformation is desirably from hypocotyls.

Agrobacterium Strains

Although any of the numerous strains of *Agrobacterium tumefaciens* capable of transferring genetic material to Brassica species can be used in combination with the other variations of the present invention, particularly improved transformation, recovery, and regeneration can be achieved by using *Agrobacterium tumefaciens* strains A281, EHA101, and K61, as well as other strains sharing common characteristics with these strains. These bacterial strains containing preferred plasmids (described later in detail), have been deposited with the American Type Culture Collection, Rockville, Md., and granted ATCC Deposit Accession No. *A. tumefaciens* A281 (pCGN200) ATCC No. 67121; *A. tumefaciens* (K61).

A number of *Agrobacterium tumefaciens* strains have been developed having different Ti-plasmids, e.g., agropine or nopaline specific. Both armed and disarmed plasmids are employed, that is, the armed plasmids contain oncogenic T-DNA that can be transferred to the plant cell and the disarmed plasmids contain no oncogenes that can be transferred to the plant cell. The strains include *Agrobacterium tumefaciens* strains A281, EHA101, and K61.

Agrobacterium A281, containing the Ti-plasmid from strain Bo542, has the following characteristics: biotype 1, agropine synthase and agropine catabolism positive, and 3-ketolactose positive. This armed strain was constructed by an in planta conjugation of wild-type Bo542 with strain A136, a C58 nopaline strain derivative cured of its Ti-plasmid and made resistance to rifampicin and nalidixic acid (E. Hood et al., *Biotechnology* (1984) 2:702–708; D. Sciaky et al., *Plasmid* (1978) 1:238–253). The virulence plasmid pTiBo542 is 249kD that contains an intact vir region and T-DNA region.

Strain EHA101 is described in Hood et al., *J. of Bacteriology* (1986) 168:1291–1301.

Strain K61 is derived from Agrobacterium strain K12 by tripartite mating with pCGN567 containing the wide host range replication system pVK102 (Knauf and Nester, *Plasmid* (1982) 8:45–54) and the left and right T-DNA borders of pTi86.

Agrobacterium strain A348, (Garfinkel et al., *Cell* (1981) 27:143–153) containing pTiA6 was transformed into strain A114 or NT1 and the resulting strain selected for octopine catabolism on BTB media (Hooykaas et al., *J. Gen. Microbiol.* (1979) 110:99–109) was named K12.

The Agrobacterium to be employed as the transformation system is conveniently transformed with a wide-host-range plasmid that can shuttle DNA from *E. coli* into Agrobacterium. This is achieved by having a P-1 incompatibility plasmid replicon, e.g., RK2, and a plasmid replicon capable of providing multicopies in *E. coli*, usually at least 5, preferably at least 10, and up to 200 copies in *E. coli*. The wide-host-=range plasmid will be characterized by having at least one T-DNA border sequence, particularly the right border sequence, or conveniently having both border sequences separated in one direction by the various constructs intended to be integrated into the plant species genome. The Agrobacterium strain may have either a disarmed Ti- or Ri-plasmid, as indicated above. The plasmid pCGN200 can be transformed into *A. tumefaciens* and detected by kanamycin resistance. Plant cells may the be cocultivated with the *A. tumefaciens* transformant, grown and selected for resistance to a biocide and expression of the desired gene(s) and can be monitored by Southern and Western blots, immunoassays, and the like. Of particular interest are markers which impart biocide resistance to plant cells and plants, so that the transformed plant species can be efficiently selected.

The Transformation Process

The transformed plant cells may be cells in culture, cells present as a disorganized mass in a callus, cells organized as leaf explants, shoot cultures, seeds, fruits, leaves, roots, or cells organized as whole plant. Hypocotyl segments are particularly preferred as target cells for forming the transformed plant cells as an enhanced transformation and recovery rate results from the use of hypocotyl segments. A hypocotyl is the part of the axis, or stem, below the cotyledons in the embryo of a plant.

The Agrobacterium strain will include on a plasmid, either the Ti-plasmid or the wide host range plasmid, a foreign construct, which foreign construct is destined to be transferred to the plant cell. As a result of such transfer, the foreign construct will normally be present in all or substantially all of the cells of the plant tissue after transformation and regeneration, but expression may be limited to particular cells or particular stages in the development of the plant. The foreign construct will include transcriptional and translational initiation and termination signals, with the initiation signals 5' to the gene of interest and the termination signals 3' to the gene of interest in the direction of transcription.

The transcriptional initiation region which includes the RNA polymerase binding site (promoter) may be native to the plant host or may be derived from an alternative source, where the region is functional in the Brassica host. A wide variety of transcriptional initiation regions may be employed, including those which are endogenous to Brassica or specific Brassica species, e.g. *napus*, or exogenous to Brassica, that is, comes from a cellular source other than a Brassica species cell. The sources of such transcriptional initiation regions may include other plant species, plant viruses, and bacterial plasmids, such as the Ti- or Ri-plasmids, particularly the T-DNA genes which are functional in plant cells. The transcriptional initiation regions may be constitutive or regulatable. Regulatable genes may be regulatable by external signals, including physical signals such as light and heat, chemical signals, such as metabolites, or cell differentiation signals, such as root-specific, leaf-specific, seed-specific, etc., or stress-related signals, etc. A preferred promoter region is the 35S promoter from cauliflower mosaic virus. This promoter is well known but has not been used previously with Brassica.

The 3' termination region may be derived from the same gene as the transcriptional initiation region or a different gene. For example, where the gene of interest has a transcriptional termination region functional in a Brassica species, that region may be retained with the gene.

An expression cassette can be constructed which will include the transcriptional initiation region, the gene of interest under the transcriptional regulational control of the transcriptional initiation region, the initiation codon, the coding sequence of the gene (with or without introns), and the translational stop codons, and will be followed by the transcriptional termination region (which will include the terminator and may include a polyadenylation signal sequence and other sequences associated with transcriptional termination). The direction is 5'-3' in the direction of transcription. The cassette will usually be less than about 10 kD, frequently less than about 6 kD, usually being at least about 1 kD, more usually being at least about 2 kD.

The gene of interest may be derived from a chromosomal gene, cDNA, a synthetic gene, or combinations thereof. Where the expression product of the gene is to be located in other than the cytoplasm, the gene will usually be constructed to include particular amino acid sequences which result in translocation of the product to a particular site, which may be an organelle (such as the chloroplast, mitochondrion or nucleus) or the cell plasma membrane, or the product may be secreted into the periplasmic space or into the external environment of the cell. Various secretory leaders, membrane integrator sequences, and translocation sequences (transit peptides) for directing the peptide expression product to a particular site are described in the literature. See, for example, Cashmore et al., *Biotechnology* (1985) 3:803–808; Wickner and Lodish, *Science* (1985) 230:400–407.

Genes of interest for use in Brassica species include a wide variety of phenotypic and non-phenotypic properties. Among the phenotypic properties are enzymes which provide for resistance to stress, such as dehydration resulting from heat and salinity, resistance to insects, herbicides, toxic metal or trace elements, or the like. Resistance may be as a result of a change in the target site, an enhancement of the amount of the target protein in the host cell, an increase in one or more enzymes involved with the biosynthetic pathway to a product which protects the host against the stress, or the like. Genes may be obtained from prokaryotes or eukaryotes, including but not limited to bacteria, fungi (e.g., yeast), viruses, plants, or mammals or may be synthesized in whole or in part. Illustrative genes include glyphosate resistance 3-enolpyruvylphosphoshikimate synthase gene, nitrilase, genes in the proline and glutamine biosynthetic pathway, and metallothioneins. Other genes of interest may be involved with regulation of growth, such as manipulations of source/sink (carbon partitioning) relations, hormonal regulation; resistance to herbicides, such as phenmedipham; production of male sterility; regulation of photosynthetic efficiency, such as altering the efficiency of RuBP carboxylase; control of the quality of the plant taste or nutritional value; altering oil or protein profile, yield, or quality; or reduction of specific undesirable metabolites such as glucosinolates or extremely long chain fatty acids e.g., $C_{22}$ fatty acids.

Instead of an expression cassette, one may have a transcription cassette, where the RNA sequence which is produced is complementary to an endogenous transcriptional product. The complementary or anti-sense sequence may be to an open reading frame, or a non-coding region, such as an intron or a 5'-non-coding leader sequence. In this way, the expression of various endogenous products may be modulated.

One or more cassettes may be involved, where the cassettes may be employed in tandem for the expression of independent genes which may express products independently of each other or may be regulated concurrently, where the products may act independently or in conjunction.

Where the expression cassette is to be transformed into plant cells by means of Agrobacterium, the cassette will be bordered by the right and optionally left T-DNA borders. These borders may be obtained from any Ti- or Ri-plasmid and may be joined to the expression cassette by conventional means. The expression cassette may be constructed so as to be directly transferred from a plasmid other than a Ti- or Ri-plasmid or may become integrated into the T-DNA region of a Ti- or Ri-plasmid through homologous recombination. Thus, the expression cassette could have DNA sequences at one or both borders of the expression cassette homologous with sequences present in the T-DNA region of the Ti- or Ri-plasmid.

The expression cassette will normally be carried on a vector having at least one replication system. For convenience, it is common to have a replication system functional in *E. coli*, such as ColE1, pSC101, pACYC184, or the like. In this manner, at each stage after each manipulation the resulting construct may be cloned and sequenced, and the correctness of the manipulation can be determined. In addition to or in place of the *E. coli* replication system, a broad host range replication system may be employed, such as the replication systems of the P-1 incompatibility plasmids; e.g., pRK290. These plasmids are particularly effective with armed and disarmed Ti-plasmids for transfer of T-DNA to the plant species host.

In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant species host. The markers may be protection against a biocide, such as antibiotics, toxins, heavy metals, or the like, or may function by complementation, imparting prototrophy to an auxotrophic host. Various genes which may be employed include neomycin phosphotransferase (NPTII; also known as APHII), hygromycin phosphotransferase (HPT), chloramphenicol acetyltransferase (CAT), nitrilase, and gentamicin resistance genes. For plant host selection, markers of particular interest include NPTII, providing kanamycin resistance of G418 resistance; HPT, providing hygromycin resistance; CAT, providing chloramphenicol resistance; mutated AroA gene, providing glyphosate resistance; etc.

The various fragments comprising the various constructs, expression cassettes, markers, and the like may be introduced consecutively by restriction enzyme cleavage of an appropriate replication system and insertion of the particular construct or fragment into the available site. After ligation and cloning the vector may be isolated for further manipulation. All of these techniques are amply exemplified in the literature and find particular exemplification in Maniatis et al., *Molecular Cloning: A Laboratory Manual*, Cold Spring Harbor Laboratory, Cold Spring Harbor, N.Y., 1982.

Once the vector is complete, the construct may now be introduced into plant cells. Techniques for transforming plant cells include microinjection, direct DNA uptake using polyethylene glycol, electroporation, viral infection, and transformation with Agrobacterium. In accordance with the subject invention, a functional method has been developed for transformation of Brassica cells employing Agrobacterium. This technique provides a methodology for the transformation of plant species with foreign genes in an efficient manner, so as to provide a rapid technique for transforming plant cells and regeneration of plants in an efficient reproducible manner.

Target Tissues

Although the prior art teaches that Brassica can be regenerated from numerous plant tissues, hypocotyls have been found to provide the greatest efficiency of transformation. Other plant parts such as leaf explants, may be used in conjunction with the subject selection and regeneration medium. However, use of hypocotyl tissue represents a preferred embodiment of the present invention.

Sterile seeds are preferably employed as a source for Brassica hypocotyls. Surface sterilized leaf pieces form 3-week-old plants of sterile grown hypocotyls of *Brassica napus* cv Westar both regenerate readily. The cut surfaces of these explants provides an ideal Agrobacterium target.

Any Brassica species can be used in the practice of the present invention such as *B. napus* (rape seed and rutabaga), *B. oleraceae* (cabbage, broccoli, brussel sprouts and other oleracea varieties), *B. juncea* (indian mustard), *B. campestris* (turnip rape), and the like.

Use of Feeder Cells During Transformation

Feeder cells can be used in the transformation process. The cells of the feeder plates act as a nurse culture for the Brassica explant as well as enhancing the efficiency of the transformation rate. In general tobacco feeder cells are used for ease of manipulation. Other feeder cells could be employed, particularly Brassica feeder cells in the form of a fine suspension.

The feeder plates are prepared by employing a plant suspension culture (e.g., Nicotiana cells grown in Murashige minimal organic medium (Flow Lab.) supplemented with 0.2 mg/l 1 2,4-dichlorophenoxyacetic acid and 0.1 mg/l kinetin) on a soft agar medium, generally having from about 0.5 to 1% agar and containing an appropriate growth medium, such as Gamborg, Miller and Ojima salts (B5 salts) ref. Gamborg et al., *Exp. Cell. Res.* (1968) 50:151–158, a carbon source, e.g., surcrose (3%), and appropriate amounts of growth substances, i.e., auxins, such as 2,4-dichlorophenoxyacetic acid (2,4-D), kinetin and vitamins (such as thiamine), with the medium appropriately buffered in the range from 5 to 6, preferably about 5.5. 2,4-D and kinetin concentrations are 1 mg/l. The final concentration of the vitamins and supplements is as follows: Inositol (100 mg/l), Nicotinic acid (1 mg/l), Pyridoxine HCl (1 mg/l), Thiamine HCl (10 mg/l). Desirably, the feeder plates are prepared prior to being used, usually 24–48 hours before being used.

The feeder plates are covered with a porous cover to prevent the feeder cells from coming into contact with the Brassica leaf or shoot explants. This porous cover allows the explants to be bathed in conditioned medium. This can be readily achieved employing a sterile filter paper disk. The explants are then allowed to preincubate, followed by transfer to a broth culture of the Agrobacterium strain containing the construction for integration and having the genetic capability for transfer of the construct into the plant cells. Generally, the number of bacteria is from about $10^7$ to $10^9$/ml (final concentration). The contact time with the bacteria in the bacterial broth culture, e.g., MG/L (same as LBMG; see Garfinkel et al., *J. Bacteriol.* (1980) 144:732–743), is preferably about 30 minutes to 1 hour, although longer or shorter times may be used. The explants are then transferred from the bacterial broth, excess surface liquid is removed, and the sections are returned to the feeder plates. Bacterial co-cultivation on the feeder plates is for at least 12 hours and not more than 3 days, averaging 1–2 days.

Selection and Regeneration Procedures

It has been found that use of a low-carbon-source medium during the regeneration procedure following co-cultivation of the Brassica cells with the transforming bacteria results in enhanced recovery and regeneration. Use of a low-carbon-source medium is believed to operate by forcing the cultured tissues to become dependent on other sources of energy, possibly photosynthesis. A low-carbon-source medium is one that contains less than 2% by weight sucrose or the equivalent of a 2% by weight sucrose solution in caloric value. Other carbon sources (e.g., mono- or di-saccharides) may give a similar effect provided that they provide the same caloric value. A typical salt and vitamin mixture is employed in conjunction with cytokinins for regeneration media.

After the 1–2 day co-cultivation with the bacteria described above, the explants are typically transferred to a Brassica callus media (which preferably contains B5 salts and vitamins, 1 mg/ 2,4-D and kinetin, 3% sucrose). Cytokinins may be excluded and their absence enhances regeneration frequency. The callus forming medium contains a bacteriocide, e.g., carbenicillin (500 mg/L) and a selective agent may be applied. For example, with the kanamycin resistance gene (neomycin phosphotransferase, NPTII) as the selective marker, kanamycin at a concentration of from about 10 to 200 mg/l may be included in the medium. Typical concentrations for selection are 10–50 mg/l although some transformants may be resistance to 200 mg/l kanamycin. The tissue is grown upon this medium for a period of 1 to 3 weeks, preferably about 7 days.

After this time the callusing explants are transferred to Brassica regeneration medium. This medium contains Gamborg, Miller and Ojima B5 salts and vitamins as described below, 1% sucrose, 3-benzyladenine (3 mg/l), zeatin (1 mg/l) 0.6% purified agar (Phytagar, Gibco), and carbenicillin at 500 mg/l. At this stage a selective agent may be applied. Shoot formation begins in about 3–6 weeks depending on treatment and co-cultivation conditions. Kanamycin-resistant callus, which is also potentially regenerable, grows in a similar time. Both regenerants and transformed callus are removed and regularly (every other week) transferred to fresh B5 medium containing the other components described immediately above. Failure to perform regular transfers results in loss of transformants and depression of apparent transformation rate.

The Brassica transformation and regeneration system described above has been found to be rapid and efficient. A sufficient percentage of the co-cultivated explants are transformed in order to provide an economic system for transforming Brassica.

The following examples are offered by way of illustration and not by way of limitation.

EXAMPLES

*E. coli* strain MM294 (Hanahna, *J. Mol. Biol.* (1983) 116:557–580) was used as the host for binary vectors containing the pRK290 type replicon. Strain K12 was generated by transforming pTiA6 into strain A114 (NT1) (Nester and Kosuge, *Ann. Rev. Microbiol.* (1981) 35:531; Hoekema et al., *Nature* (1983) 303:179). Agrobacterium strain A281 was generated by conjugating wild-type Bo542, with strain A136 (D. Sciaky, et al., *Plasmid* (1978) 1:238–253). Agrobacterium strain EHA101 is described by Hood et al., *J. of Bacteriology* (1986) 168:1291–130).

Levels of antibiotics used with *E. coli* in mg/l were 30 for kanamycin, 50 for chloramphenicol, 300 for penicillin, 10 for tetracycline, and 20 for gentamicin. Unless otherwise indicated, levels of antibiotics used with Agrobacterium in mg/l were 100 for kanamycin or gentamicin and 50 for carbenicillin or chloramphenicol.

Laboratory Procedures

Restriction enzymes and T4 ligase were obtained from commercial sources and used according to manufacturers' recommendations. Standard methods of cloning and molecular analysis were performed as described in Maniatis et al., supra.

Designations of media used in these procedures are as follows:

B5 medium means that described by Gamborg, Miller and Ojima, *Exp. Cell Research* (1968) 50:151–158.

| B5 Salts are: | mg/l |
| --- | --- |
| Ammonium sulfate | 134.0 |
| Boric acid | 3.0 |
| Calcium chloride | 150.0 |
| Cobaltous chloride | 0.025 |
| Cupric sulfate | 0.025 |
| Ferrous sulfate | 27.8 |
| Magnesium sulfate | 250.0 |
| Manganese sulfate | 10.0 |
| Potassium iodide | 0.75 |
| Potassium nitrate | 2500.0 |
| Sodium ethylenediamine tetraacetate | 37.3 |
| Sodium molybdate | 0.25 |
| Sodium dihydrogen phosphate | 150.0 |
| Zinc sulfate | 2.0 |

Unless otherwise stated B5 medium contains 3% sucrose weight/volume.

| B5 vitamins and supplements are: | mg/l |
| --- | --- |
| myo-Inositol | 100.0 |
| Nicotinic acid | 1.0 |
| Pyridoxine HCl | 1.0 |
| Thiamine HCl | 10.0 |

The designation B5 0/1/1 means B5 medium, 3% sucrose, 1 mg/l 2,4-D, 1 mg/l kinetin and the designation B5 0/1/0 is the same except the kinetin is not included. The growth substance concentrations are denoted by the / (slash) notation, with the concentration of 3 growth substances in mg/l being denoted. In order these are indole-3-acetic acid/2,4-K/kinetin.

The designation B5BZ 1% means B5 salts, vitamins and supplements plus 1% w/v sucrose, 3 mg/l benzyl adenine and 1 mg/l zeatin. B5BZ 1% is used here as regeneration and selection medium for kanamycin resistance of Brassica tissue.

EXAMPLE I

Construction of pCGN587

The BglII-SmaI fragment of Tn5 containing the entire structural gene for APHII (Jorgensen et al., *Mol. Gen.* (1979) 177:65) was cloned into pUC8 (Vieira and Messing, *Gene* (1982) 19:259), converting the fragment into a HindIII-EcoRi fragment, since there is an EcoRI site immediately adjacent to the SmaI site. The PstI-EcoRI fragment containing the 3' portion of the APHII gene was then combined with an EcoRI-BamHI-SalI-PstI linker into the EcoRI site of pUC7 (pCGN546W). Since this construct does not confer kanamycin resistance, kanamycin resistance was obtained by inserting the BglII-PstI fragment of the APHII gene into the BamHI-PstI site (pCGN546X). This procedure reassembles the APHII gene, so that EcoRI sites flank the gene. An ATG codon was upstream from and out of reading frame with the ATG initiation codon of APHII. The undesired ATG was avoided by inserting a SauIIIA-PstI fragment from the 5'-end of APHII, which fragment lacks the superfluous ATG, into the BamHI-PstI site of pCGN546W to provide plasmid pCGN550.

The EcoRI fragment containing the APHII gene (1 ATG) was then cloned into the unique EcoRI site of pCGN451, which contains an octopine synthase cassette for expression to provide pCGN552 (1 ATG).

Plasmid pCGN451 includes an octopine cassette which contains about 1556 bp of the of the 5' non-coding region fused via an EcoRI linker to the 3' non-coding region of the octopine synthase gene of pTiA6. The pTi coordinates are 11,207 to 12,823 for the 3' region and 13,643 to 15,208 for the 5' region as defined by Barker et al., *Plant Mol. Biol.* (1983) 2:325.

The 5' fragment was obtained as follows. A small subcloned fragment containing the 5' end of the coding region, as a BamHI-EcoRI fragment was cloned in pBR322 as plasmid pCGN407. The BamHI-EcoRI fragment has an XmnI site in the coding region, while pBR322 has two XmnI sites. pCGN407 was digested with XmnI, resected with Bal31 nuclease and EcoRI linkers added to the fragments. After EcoRI and BamHI digestion, the fragments were size fractionated, the fractions cloned and sequenced. In one case, the entire coding region and 10 bp of the 5' non-translated sequences had been removed leaving the 5' non-transcribed region, the mRNA cap site and 16 bp of the 5' non-translated region (to a BamHI site) intact. This small fragment was obtained by size fractionation on a 7% acrylamide gel and fragments approximately 130 bp long eluted. This size fractionated DNA was ligated into M13mp9 and several clones sequenced and the sequence compared to the known sequence of the octopine synthase gene. The M13 construct was designated pI4, which plasmid was digested with BamHI and EcoRI to provide the small fragment which was ligated to a XhoI to BamHI fragment containing upstream 5' sequences from pTiA6 (Garfinkel and Nester, *J. Bacteriol.* (1980) 144:732) and to an EcoRI to XhoI fragment containing the 3' sequences. The resulting XhoI fragment was cloned into the XhoI site of a pUC8 derivative, designated pCGN426. This plasmid differs from pUC8 by having the sole EcoRI site filled in with DNA polymerase I, and having lost the PstI and HindIII site by nuclease contamination of HincII restriction endonuclease, when a XhoI linker was inserted into the unique HincII site of pUC8. The resulting plasmid pCGN451 has a single EcoRI site for the insertion of protein coding sequences between the 5' non-coding region (which contains 1,550 bp of 5' non-transcribed sequences including the right border of the T-DNA, the mRNA cap site and 16 bp of 5' non-translated sequence) and the 3' region (which contains 267 bp of the coding region, the stop codon, 196 bp of 3' non-translated DNA, the polyA site and 1,153 bp of 3' non-transcribed sequence).

The resulting plasmid pCGN451 having the ocs 5' and ocs 3' in the proper orientation was digested with EcoRI and the EcoRI fragment from pCGN451 containing the intact kanamycin resistance gene inserted into the EcoRI site to provide pCGN552 having the kanamycin resistance gene in the proper orientation.

This ocs/KAN gene was used to provide a selectable marker for the trans-type binary vector pCGN587.

The 5' portion of the engineered octopine synthase promoter cassette consists of TiA6 DNA from the XhoI fragment at bp 15208–13644 (Barker's numbering as in Barker et al., supra), which also contains the T-DNA boundary sequence (border) implicated in T-DNA transfer. In the plasmid pCGN587, the ocs/KAN gene from pCGN552 provides a selectable marker as well as the right border. The left boundary region was recloned from the HindIII-EcoI fragment as a KpnI-EcoRI fragment in pCGN565 to provide pCGN580. pCGN565 is a cloning vector based on pUC8-Cm, but containing pUC18 linkers. pCGN580 was linearized with BamHI and used to replace the smaller BglII fragment of pVCK102 (Knauf and Nester, *Plasmid* (1982) 8:45), creating pCGN585. By replacing the smaller SalI fragment of PCGN585 with the XhoI fragment from pCGN552 containing the ocs/KAN gene, pCGN587 was obtained.

Construction of pCGN200

To construct pCGN200, a plasmid containing a full-length promoter from CaMV (35S) and kanamycin gene as a selectable marker, pCGN167 was recombined into a binary vector, pCGN587.

To construct pCGN167, the AluI fragment of CaMV (bp 7144–7735) (R. Gardner et al., *Nucl. Acid, Res.* (1981) 9:2871–2888) was obtained by digestion with AluI and cloned into the HincII site of M13mp7 (Vieira, et al., *Gene* (1982) 19:259) to create C614. An EcoRI digest of C614 produced the EcoRI fragment from C614 containing the 35 S promoter which was cloned into the EcoRI site of pUC8 (Vieira et al., *Gene* (1982) 19:259) to produce pCGN146.

To trim the promoter region, the BglII site (bp 7670) was treated with BglII and Bal31 and subsequently a BglII linker was attached to the Bal31 treated DNA to produce pCGN147.

pCGN148a containing a promoter region, selectable marker (KAN with 2 ATG's) and 3' region, was prepared by digesting pCGN528 (see below) with BglII and inserting the BamHI-BglII promoter fragment from pCGN147. This fragment was cloned into the BglII site of pCGN528 so that the BglII site was proximal to the kanamycin gene of pCGN528.

The shuttle vector used for this construct, pCGN528, was made as follows. pCGN525 was made by digesting a plasmid containing Tn5 which harbors a kanamycin gene (Jorgenson et al., *Mo. Gen.* (1979) 177:65) with HindIII-BamHI and inserting the HindIII-BamHI fragment containing the kanamycin gene into the HindIII-BamHI sites in the tetracycline gene of pACYC184 (Chang & Cohen, *J. Bacteriol.* (1978) 134:1141–1156). pCGN526 was made in inserting the BamHI fragment 19 of pTiA6 (Thomashaw et al., *Cell* (1980) 19:729–739) into the BamHI site of pCGN525. pCGN528 was obtained by deleting the small XhoI fragment from pCGN526 by digesting with XhoI and religating.

pCGN149a was made by cloning the BamHI-kanamycin gene fragment from pMB9KanXXI into the BamHI site of pCGN148a.

pMB9KanXXI is a pUC4K variant (Vieira & Messing, *Gene* (1982) 19:259–268) which has the XhoI site missing but contains a functional kanamycin gene from Tn903 to allow for efficient selection in Agrobacterium.

pCGN149a was digested with BglII and SphI. This small BglII-SphI fragment of pCGN149a was replaced with the BamHI-SphI fragment from MI (see below) isolated by digestion with BamHI and SphI. This produces pCGN167, a construct containing a full length CaMV promoter, 1ATG-kanamycin gene, a 3' end and the bacterial Tn903-type kanamycin gene. MI is an Eco RI fragment from pCGN546X (see construction of pCGN587) and was cloned into the EcoRI cloning site of M13mp9 in such a way that the PstI site in the 1ATG-kanamycin gene was proximal to the polylinker region of M13mp9.

pCGN200 was made by transforming an *E. coli* strain C2110 (polA1) containing the binary vector pCGN587 with pCGN167. pCGN167 recombined in vivo to make pCGN200. There are two regions of direct DNA homology by which recombination could have occurred. In this case recombination took place between the pUC origin of replication regions carried by pCGN167 and pCGN587. Recombinants were selected by kanamycin resistance (deFromard et al., *Biotechnology*, May 1983, pp. 262–267).

pCGN200 was introduced into *Agrobacterium tumefaciens* A281 and K12 by mating. Bacterial matings were performed using two *E. coli* strains and one Agrobacterium strain. One *E. coli* strain (MM294) harbored pRK2073 which provided mobilization functions, and the other strain (C2110) carried the plasmid with a kanamycin resistance marker to be transferred into Agrobacterium. The two *E. coli* strains were grown overnight at 37° C. with shaking in LB broth. The Agrobacterium strain was grown overnight at 28° C. in MG/L broth. Fifty microliters of each of the three strains were mixed on a nitrocellulose filter and placed on an MG/L plate. The plate was incubated at 28° C. for 3 days. The mixture was then streaked onto an AB minimal medium (D. M. Glover, *DNA Cloning Volume II* (1985) p. 78) supplemented with 100 µg/ml kanamycin and 100 µg/ml streptomycin and incubated at 28° C. for two days. Streptomycin was included to kill the two *E. coli* strains. Single colonies were picked and purified by two more streakings on the above medium.

Construction of strain K61

The Ti plasmid pTiA6 was isolated from Agrobacterium strain A348 (Garfinkel et al., *Cell* (1981) 27:143–153) and used to transform Agrobacterium strain A114 (also designated NT1) (Currier and Nester, *J. Bacteriol.* (1976) 126:157–165). Octopine catabolism was selected for on BTB media (Hooykaas et al., *J. Gen. Microbiol.* (1979) 110:99–109). This strain was named K12.

The left T-DNA border region of pTiA6 (bp 602 to 2212 by the numbering system of Barker et al., supra) was cloned as a HindIII to SmaI fragment in the phage vector M13mp9 (pCGN501). The M13mp9 linker architecture provides the fragment as a HindIII to EcoRi fragment. The right T-DNA border region of pTiA6 (bp 13362 to 15208, Barker et al., supra) was subcloned as a EcoRI to XhoI fragment into M13mp9 cut with enzymes EcoRI and SalI (pCGN502). This piece could then be excised as a EcoRI to HindIII fragment. The plasmids pCGN501 and pCGN502 were digested with HindIII and EcoRI and ligated to pUC8 DNA previously cut with just HindIII. Selection of white penicillin resistant colonies yielded an isolate containing the pUC8 vector with a 3.5 kbp HindIII fragment containing the left and right T-DNA borders of pTiA6 in the natural orientation (pCGN503). This 3.5 kpb HindIII fragment containing T-DNA borders was then transferred into the HindIII site of pVK102 (pCGN506). The wide host range cloning vector pVK102 (also designated pVCK102) has been described (Knauf and Nester, *Plasmid* (1982) 8:45–54). The orientation of the border fragment in pCGN506 relative to the pVK102 vector is the left T-DNA border region proximal to the tetracycline resistance locus. pCGN506 has a unique EcoRI site and a unique BamHI site in between the left and right border regions, i.e., such that any inserts wold be oriented in the natural orientation. The plasmid pCGN567 was constructed by ligating the BamHI fragment of pUC4K bearing a kanamycin resistance determinant into the BamHI site of pCGN506. Thus, pCGN567 codes for both tetracycline and kanamycin resistance.

The plasmid pCGN567 was mated into Agrobacterium strain K12 by the tripartite method (Ditta et al., *Proc. Natl.*

*Acad. Sci, USA* (1981) 77:7347–7351) using kanamycin selection for transconjugant Agrobacterium on minimal media. *E. coli* bearing the plasmid pPH1J1 (Garfinkel et al., *Cell* (1981) 27:143–153) was then mated with strain K12 (pCGN567) and transconjugant Agrobacterium were selected on minimal media containing both kanamycin and gentamicin. Since pPH1J1 and pCGN567 are incompatible plasmids, it was expected that a double recombination event between two direct regions of homology with the Ti-plasmid would result in the exchange of the kanamycin resistance locus for all of the oncogenic gene loci between the border regions (for explanation of method, see Garfinkel et al., *Cell* (1981) 27:143–153). However, this did not occur. Kanamycin and gentamicin resistance Agrobacterium resulting from the introduction of pPH1JI into K12 (pCGN567) grew very slowly suggesting both pCGN567 and pPH1JI were present in an unstable situation resulting in the apparent slow growth of a colony as individual bacteria tended to shed one of the two plasmids due to incompatibility problems. By alternating growth on kanamycin-containing media and gentamicin-containing liquid media in overnight cultures, an isolate with the expected growth rates was identified. Plasmid DNA was isolated from that strain and used to transform strain A114, selecting for kanamycin resistance and tooth-picking for gentamicin sensitivity. The resulting strain of Agrobacterium, K61, therefore lacked pPH1JI. Restriction enzyme analysis of the plasmid in K61 (pTiK61) using SmaI, HpaI, EcoRI, and SalI revealed a Ti-plasmid lacking sequence corresponding to kpb 173.30 to 181 and 0.0 to 53.35 of pTiA6 (using the numbering system of Knauf and Nester, *Plasmid* (1982) 8:45–54). This explained the inability of strain K61 to utilize octopine, a trait normally encoded by pTiA6. Thus, pTiK61 represents a spontaneous deletion of pTiA6 in which the left border region is still present but the oncogenes, right T-DNA border, the $T_R$-DNA region and other loci including octopine catabolism are deleted. Regions encoding the vir region of pTiA6, namely coordinates 111 through 168 (using the numbering system of Knauf and Nester, supra) are intact in pTiK61 which represents a disarmed Ti-plasmid lacking oncogenes or functional T-DNA but containing vir genes necessary to accomplish T-DNA transfer from binary T-DNA vectors.

Construction of pCGN767

A genomic library was constructed in the λ vector EMBL4 (Fischauf et al., *J. Mol. Biol.* (1983) 170:827–842) from *B. napus* DNA digested partially with SauIIIA. Two unique napin genomic clones, designated λBnNa and λBnNb, were isolated when $4 \times 10^5$ recombinant phage were screened by plaque hybridization with a nick-translated pN1 napin cGNA probe (Crouch et al., *J. Mol. Appl. Gen.* (1983) 2:273–283).

The napin genomic clones were analyzed by restriction nuclease mapping and Southern blot hybridizations. Each phage contains just one napin gene, and only the napin gene region hybridizes to cDNA made from embryo RNA. The 3.3 kb EcoRI fragment containing the λBnNa napin gene was subcloned in pUC8 (Veiera and Messing, 1982) and designated pgNa.

An approximate 320 bp SalI fragment was cloned into the XhoI site of pgNa to create pCGN714 placing a bacterial DNA sequence as a "tag" after the stop codon of the napin coding region in pgNa. In this case, the bacterial DNA sequence consisted of a SalI restriction fragment containing the coding region of a dihydrofolate reductase (DHFR) gene. The EcoRI fragment in pgNa containing the napin gene with 300 bp of promoter and approximately 2100 bp following the napin coding region is about 3.6 kb in pCGN714.

The HindIII-EcoRI set of linkers in pUC18 (Yanisch-Perron et al., *Gene* (1985) 33:103) were transferred into pUC12Cm (Keith J. Buckley, Ph.D. Thesis, USCD, 1985) to create pCGN565 which is basically a pUC replicon linked to chloramphenicol resistance and the blue-white cloning system of pUC12. The EcoRI fragment of pCGN714 containing the tagged napin gene was transferred to the EcoRI site of pCGN565 to get PCGN723 which codes for chloramphenicol resistance rather than the penicillin resistance of pCGN714. The HindIII-EcoRI linkers of pUC8Cm (Keith J. Buckley, Ph.D., Thesis, UCSD, 1985) were transferred into HindIII-EcoRI cut pEMBL19 (Dente et al., *Nucl. Acid, Res.* (1983) 11:1645) making pCGN730a. Unlike the parent pEMBL19, pCGN730a lacks any SstI sites. The EcoRI fragment of pCGN723 containing the tagged napin gene was transferred to the EcoRI site of pCGN730a. The SstI site in the napin gene was then unique in the resulting plasmid, pCGN735.

Two 27mer oligonucleotides were synthesized on an Applied Biosystems DNA synthesizer machine. ∤A consisted of the sequence:
C-C-T-G-A-T-G-A-T-G-A-T-G-A-T-G-A-T-G-C-T-G-C-A-G-C-T
in the order of 5' to 3'. ∤B consisted of the sequence:
G-C-A-G-C-A-T-C-A-T-C-A-T-C-A-T-C-A-T-C-A-G-G-A-G-C-T-

These two oligonucleotides are partially complementary so that by annealing, they leave 3' sticky ends compatible with cloning in SstI sites. In the desired orientation, a single insert adds coding for an additional 9 amino acids, 5 of which are methionine residues. The synthetic dsDNA created by annealing oligonucleotides ∤A and ∤B was cloned into the SstI site of pCGN735. Since the oligonucleotides were not phosphorylated, the insertion of only one element was likely even through the insert was in excess to pCGN735 SstI ends. Restriction enzyme analysis of that plasmid, pCGN757, indicated that an insert was present (this and the orientation were later verified by DNA sequencing). The EcoRI fragment of pCGN757 was transferred to pCGN565 so that plasmid pCGN757c, coded for chloramphenicol resistance rather than the penicillin resistance of pCGN757.

pCGN549 was made by cloning the EcoRI (coding for gentamicin resistance) of pPH1Jl (Hirsch and Beringer, *Plasmid* (1984) 12:139) into EcoRI and PstI cut pUC9. pCGN594 was made by cutting pCGN587 with HindIII and BglII and combining with pCGN549 cut with HindIII and BamHI. This replaced the pUC replicon and chloramphenicol marker of pCGN587 with a bacterial gentamicin marker. pCGN739 was made by replacing the HindIII-BamHI fragment of pCGN594 with the HindIII-BamHI linkers of pUC18. This effectively replaced the eukaryotic selectable marker of pCGN594 with a series of unique cloning sites for insertion of other types of selectable markers. pCGN763 was made by the transfer of the HindIII-BamHI fragment of pCGN976 (obtained by insertion of a HindIII-BamHI fragment from pCGN167 into HindIII-BamHI digested pUC19 to introduce the 35S promoter, kanmycin resistance and tml 3' region) into HindIII-BamHI cut pCGN739. pCGN757c was linearized with HindII and cloned into the HindIII site of pCGN763 to create the binary vector pCGN767 which includes a bacterial gentamicin resistance marker, a chimeric eukaryotic kanamycin resistance gene (with CaMV 35A promoter and pTiA6 T-DNA tml transcription termination signals), and the tagged, engineered napin gene between pTiA6 T-DNA borders.

EXAMPLE II

Brassica Transformation

Explants from soil-grown seedlings of *Brassica napus* cv Westar (Agriculture Canada, Saskatoon, Canada) were used as primary target material. Plants were grown 3-4 weeks in a 16-8 hour light-dark cycle 220 $\mu Em^{-2}S^{-1}$ at 24° C. Partially expanded secondary leaves were excised, surface sterilized for 15 min in 1% sodium hypochlorite, and washed four times with sterile water.

Leaf discs 4 mm in diameter were cut from the sterile leaves using a cork borer. These discs were pre-incubated for 24 hours at 24° C. in darkness on a B5 medium (KC Biologicals) containing 1 mg/l 2,4-D and 1 mg/l kinetin solidified using 0.6% purified agar (Phytagar) (B5 0/1/1).

*Agrobacterium tumefaciens* (strain A281×200) was prepared overnight in MG/L broth by incubating a single colony of *Agrobacterium tumefaciens*. Bacteria were harvested at time periods of 16–36 hours. Dilutions of bacteria to concentrations of $10^6$–$10^7$ bacteria per ml were prepared in B5 0/1/1 liquid medium. Leaf explants were inoculated with bacteria by dipping into the Agrobacterium suspension and then lightly blotting them on sterile paper towels. Inoculated leaf discs were then transferred to Petri plates of B5 0/1/1 medium with 0.6% Difco Phytagar, at a density of 20 discs per plate.

The co-incubation of bacteria and leaf discs took place for periods from 12 to 48 hours. After this co-culture step, the discs were washed in liquid B5 0/1/1 medium and transferred to Petri plates containing B5 0/1/1 and 500 mg/l carbenicillin, 0.6% Difco Phytagar. These explants were cultured in light (50 $\mu Em^{-2}s^{-1}$) on this medium for 7–10 days until callus formation was evident. At this time the explants were transferred to a second medium optimized for regeneration in *Brassica napus* cv Westar. This contained B5 salts and vitamins, 3 mg/l benzyl adenine, 1 mg/l zeatin, and 1% sucrose. It was supplemented with 500 ml/l carbenicillin and 50 mg/l kanamycin sulfate. This medium was solidified using 0.7% Phytagar. Under lighted conditions (16-8 light-dark cycles at 24° C., 100 $\mu Em^{-2}s^{-1}$) the tissue began to develop green callus. Under non-selective conditions without kanamycin sulfate) numerous shoots form on this medium which can be propagated and rooted. Under selective conditions green callus and shoot formation is evident, but greatly reduced.

Under these selective conditions successful transformation events leading to kanamycin-resistant material will grow and may be scored for frequency. To assure that the primary selection pressure is for kanamycin resistance and not nutrient scavenging or insensitivity to inhibitors released from dying tissue, the explants were re-plated on the identical medium every 7–10 days.

Figure 1:
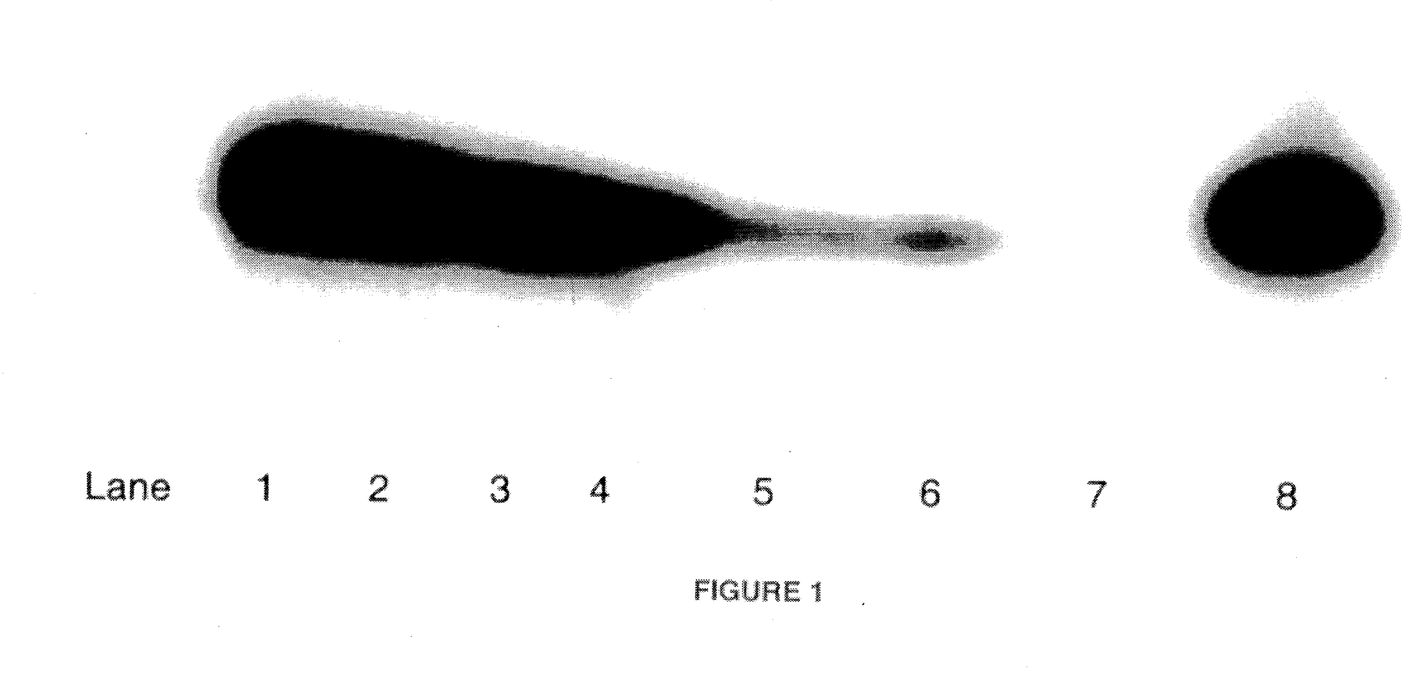
FIG. 1 is an autoradiography map created by polyacrylamide gel electrophoresis of cellular protein to demonstrate the presence of the neomycin phosphotransferase gene in transformed cells growing on selective media by showing the existence of ATP-mediated phosphorylation of kanamycin using $\gamma$-$^{32}$P-labelled ATP.
Figure 2:
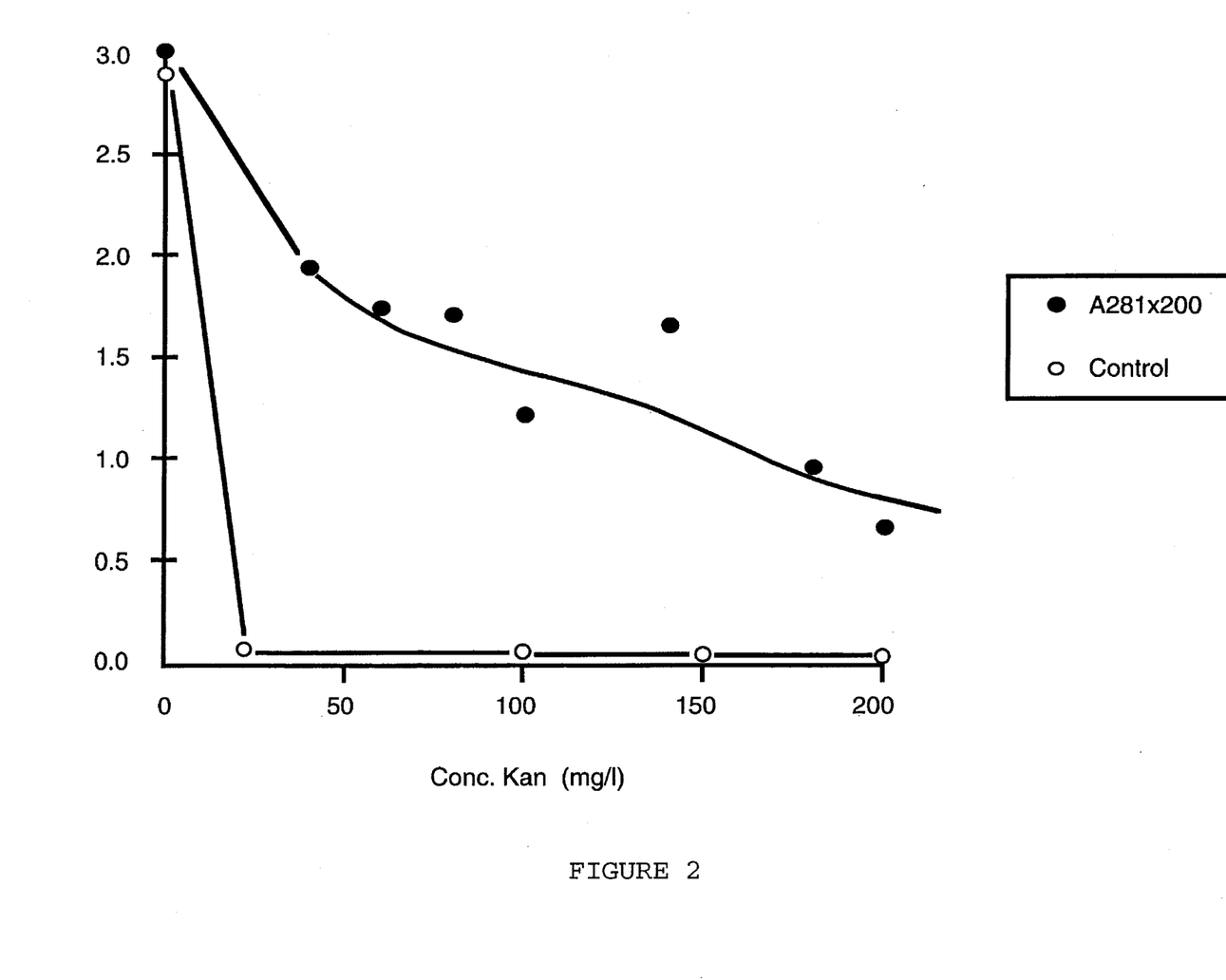
FIG. 2 is a graph showing sensitivity of transformed and untransformed Brassica tissue to kanamycin.
Figure 3A:
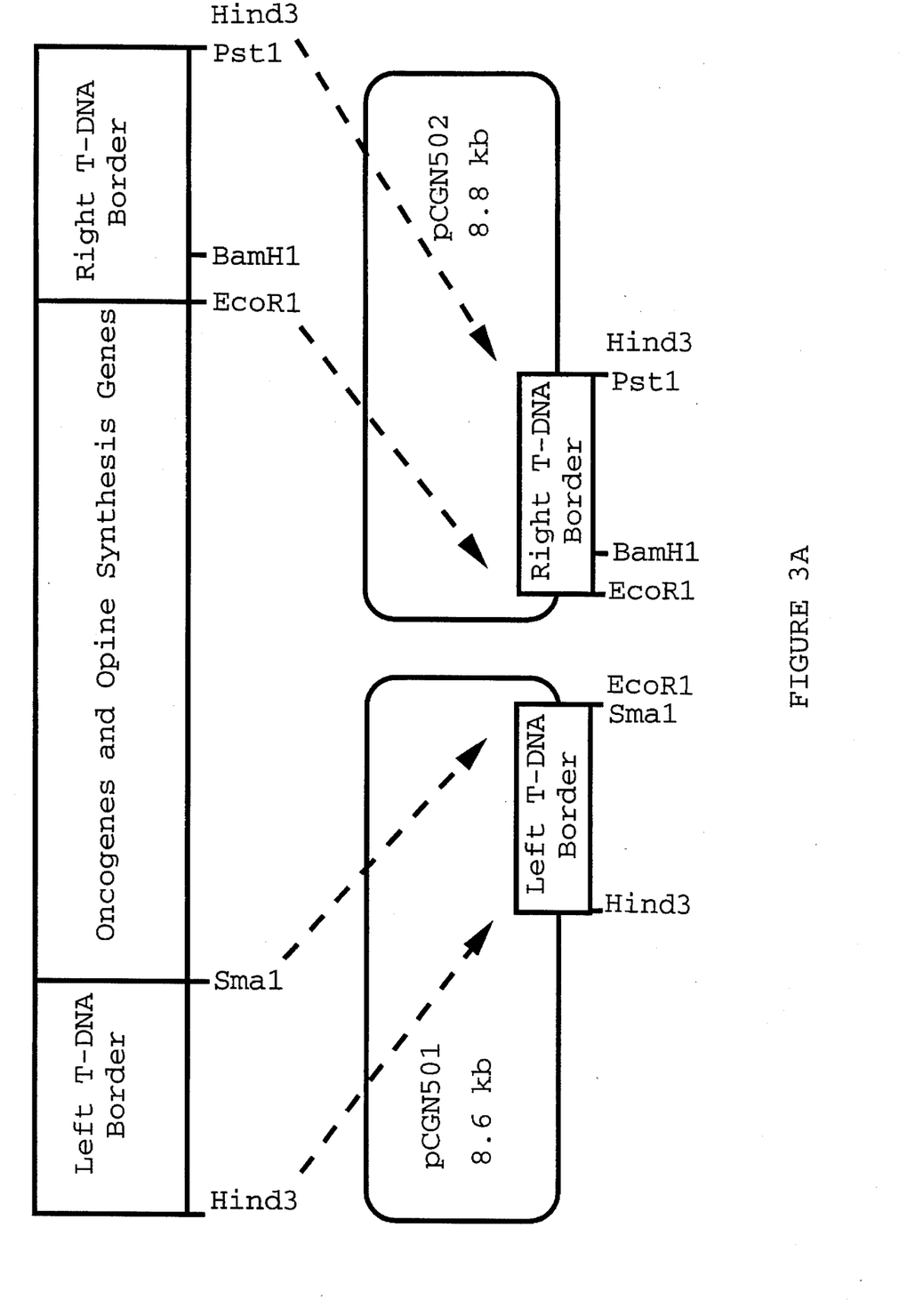
FIG. 3 is a pTiA6 T-DNA map and pathway to pTiK61.
Figure 3B:
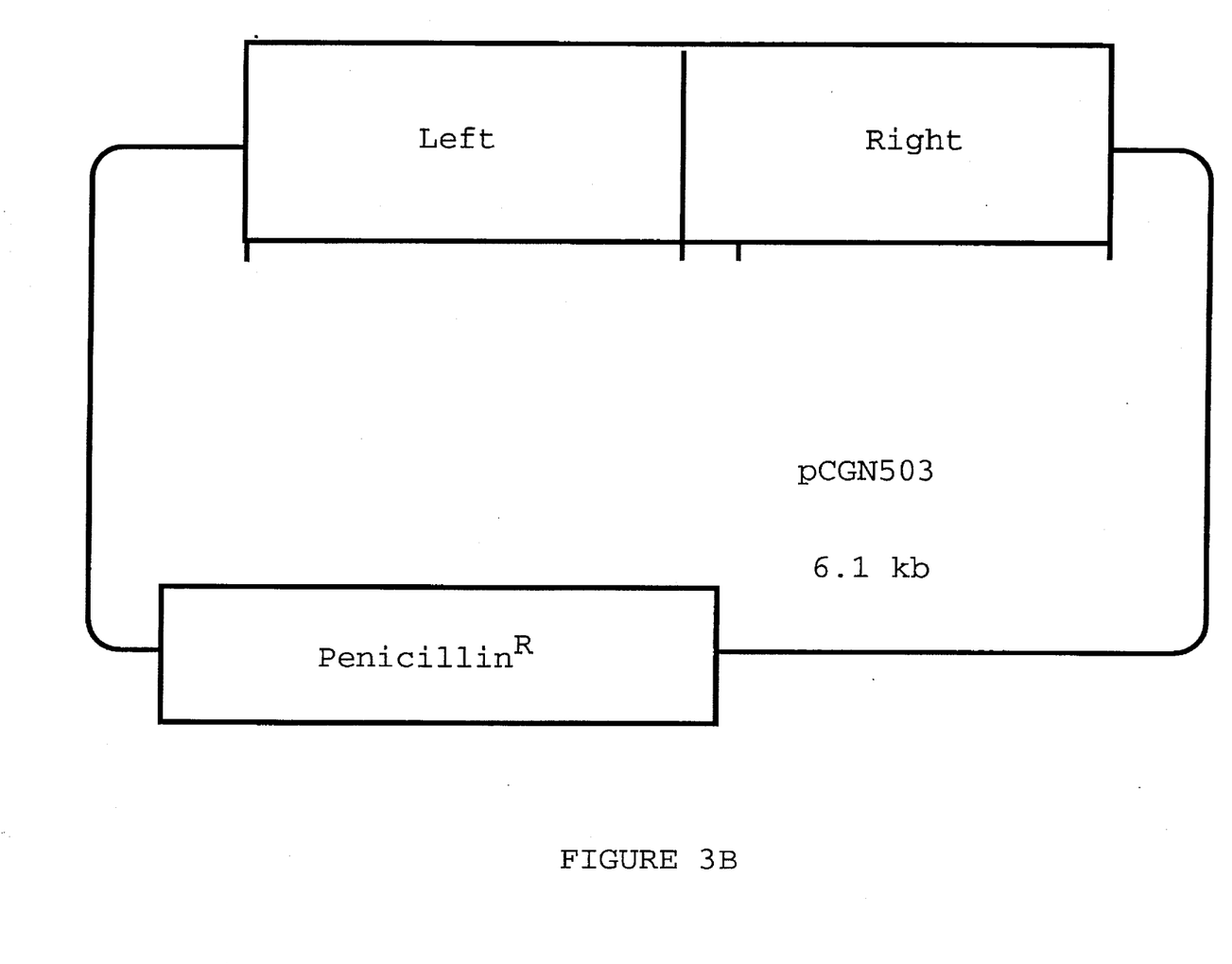
Figure 3C:
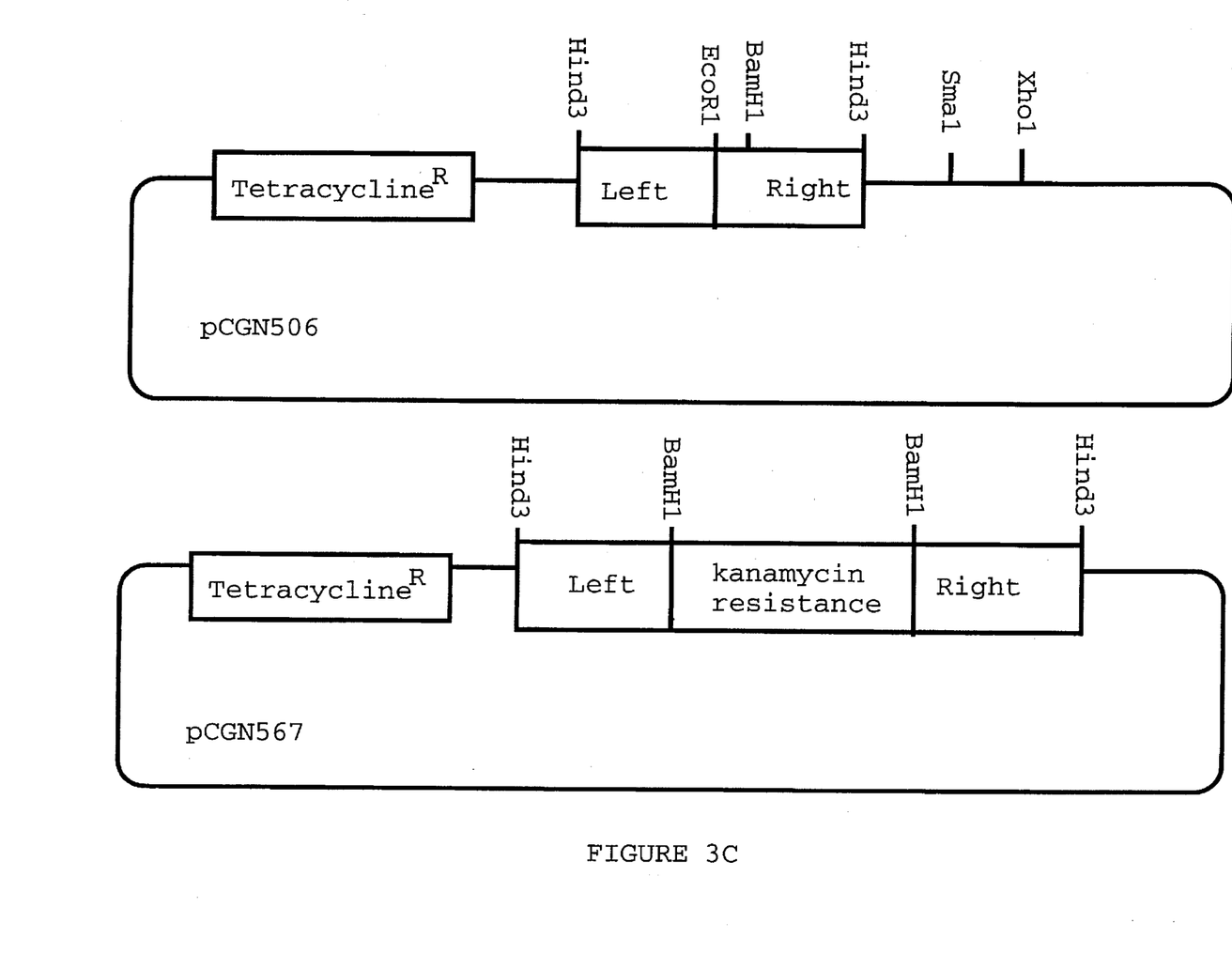
Figure 3D:
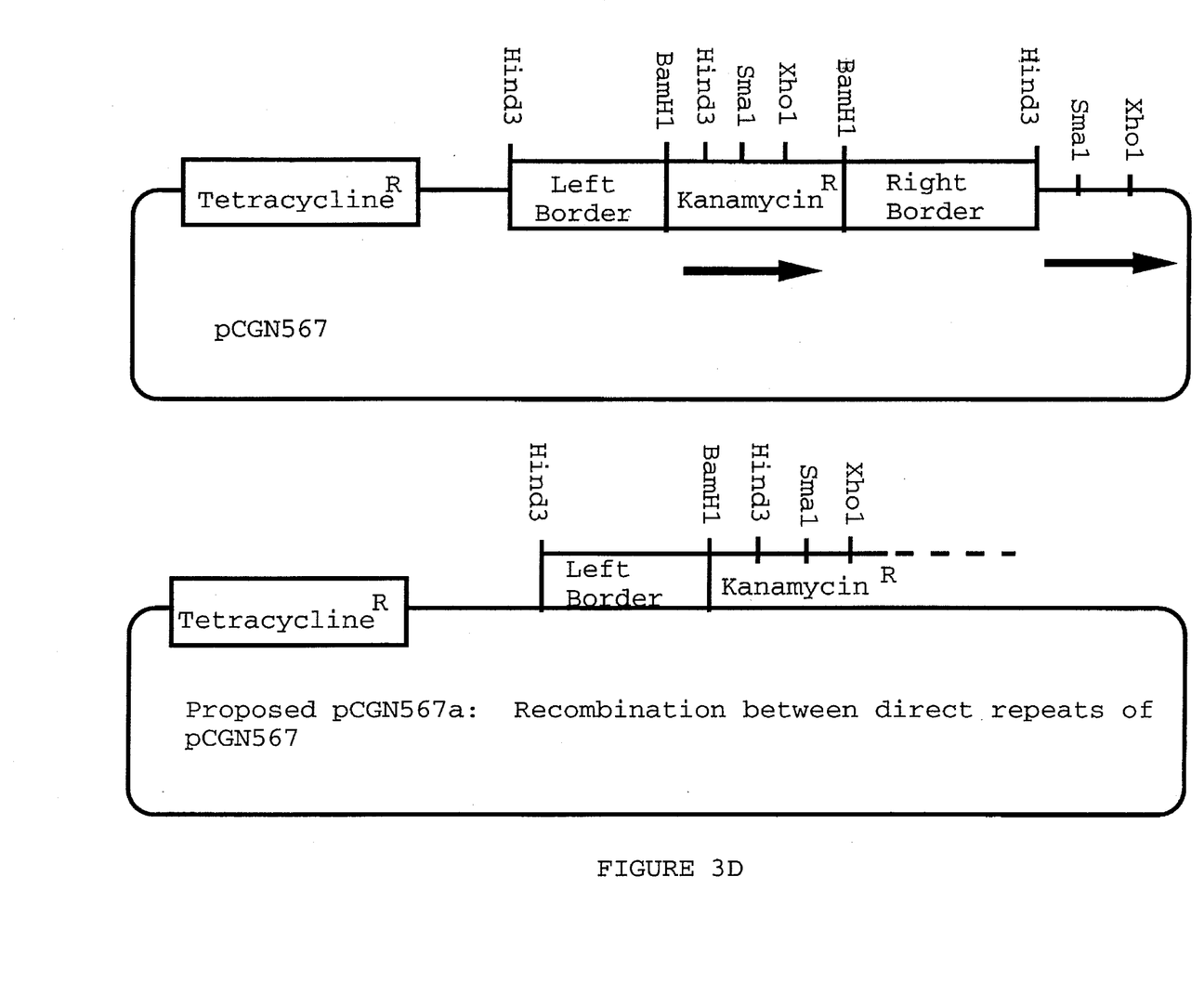
Figure 3E:
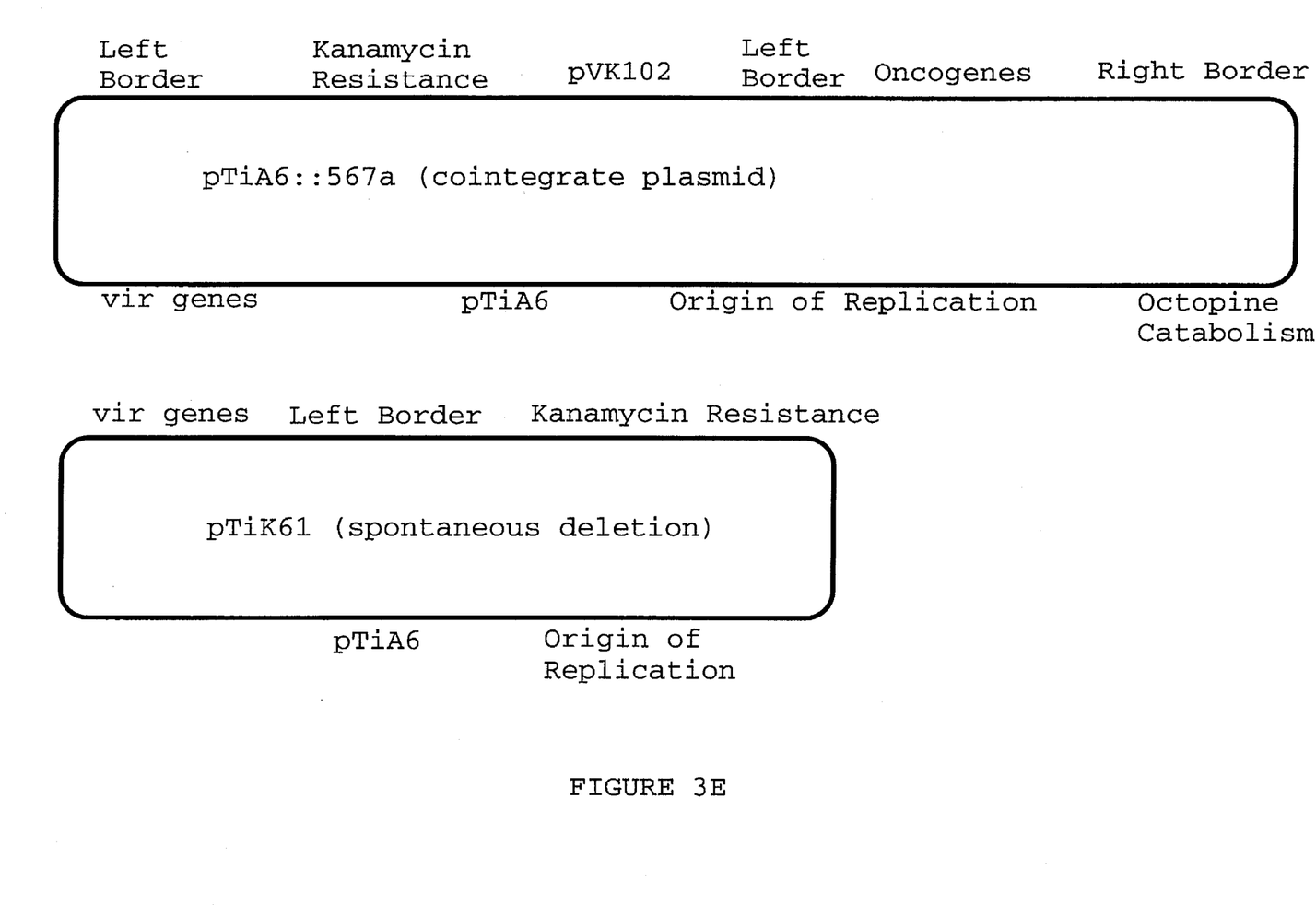

Shoots and callus growing on the kanamycin-containing medium may be tested for the expression of the neomycin phosphotransferase gene using an assay described by Reiss et al., *Gene* (1984) 30:211–218. This employs polyacrylamide gel electrophoresis to separate the enzyme from background proteins. Enzyme activity is detected in situ by ATP mediated phosphorylation of kanamycin using $\gamma$-$^{32}$P-labelled ATP. The product of the reaction is blotted onto P81 ion exchange paper which is then treated (45 min at 65° C.) with Proteinase K (1 mg/l, Sigma Chemicals) in 1% sodium dodecyl sulfate. This treatment removes much of the background radioactivity on the paper associated with $^{32}$P-labelled proteins. The phosphorylated kanamycin remains intact during the treatment. This product is then detected by autoradiography and may be quantified by scintillation counting. An example of such an assay performed on transformed, kanamycin resistance *Brassica napus* tissue is shown in FIG. 1. The phenotype of the transformant is kanamycin resistance. The level of resistance in a Brassica A281×200 transformant is shown in FIG. 2.

EXAMPLE III

Transformation may be conducted using *Agrobacterium tumefaciens* in the presence of a feeder cell layer. This may be advantageous both to help the Agrobacterium-treated tissue recover and for stimulation of transformation activity. In this embodiment the tissues are prepared as described in Example II, but then are transferred, after dipping into Agrobacterium and blotting, onto Petri plates containing feeder cells of *Nicotiana tabacum* (tobacco) suspension cells. The feeder plates are prepared by pipetting 1.0 ml of a stationary phase tobacco suspension culture onto B5 medium containing 1 mg/l of both 2,4-D and kinetin with vitamins as described above. The medium is solidified using 0.6% agar. The feeder plates are produced 24–48 hours prior to use, and the excised Brassica tissue may be pre-incubated on the feeder plate by placing a sterile Whatman 3 mm filter paper on top of the feeder layer and arranging the excised Brassica tissue on this 24 hours prior to Agrobacterium treatment.

After dipping in *Agrobacterium tumefaciens* (A281×200 or similar strain) the Brassica explants are returned to the feeder plates for a further 24∝48 hours. After this time they are transferred to B5 medium containing 1 mg/l kinetin, 1 mg/l, 2,4-D and 500 mg/l carbenicillin in agarized medium (0.6%). All other steps are identical to those described in Example II.

EXAMPLE IV

This transformation method can also be applied effectively to hypocotyl explants rather than leaf explants. All procedures for transformation of the hypocotyl explants are identical to those described above for leaf discs; however, the preparation of hypocotyl material differs.

Seeds of *Brassica napus* cv Westar were surface sterilized in a 1% sodium hypochlorite solution containing 200 μl of "Tween 20" surfactant per 500 ml of sterilant solution. After 20 minutes soaking in the sterilant the seeds were washed (4 times) with sterile distilled water and planted in sterile plastic boxes 7 cm wide, 7 cm long, and 10 cm high (Magenta) containing 50 ml of ¹⁄₁₀ concentrated B5 medium (Gamborg, Miller and Ojima, *Experimental Cell. Res.* (1968) 50:151–158) containing no growth substances and solidified with 0.6% agar. The seeds germinated and were grown at 23°–25° C. in a 16-8 hours light-dark cycle with light intensity approximately 100 $\mu Em^{-2}s^{-1}$. After 5 days the seedlings were taken under sterile conditions and the hypocotyls excised and cut into pieces of about 4 mm in length. These hypocotyl segments were then treated with all the same procedures applied to leaf disc explants in Example II.

EXAMPLE V

Seeds of *Brassica napus* cv Westar were soaked in 95% ethanol for 4 minutes. They were sterilized in 1% solution of sodium hypochlorite with 50 μl of "Tween 20" surfactant per 100 ml sterilant solution. After soaking for 45 minutes, seeds were rinsed 4 times with sterile distilled water. They were planted in sterile plastic boxes 7 cm wide, 7 cm long, and 10 cm high (magenta) containing 50 ml of ¹⁄₁₀th concentration of MS (Murashige minimal organics medium, Gibco) with added pyridoxine (50 µg/l), nicotinic acid (50 µg/l), glycine (200 µg/l) and solidified with 0.6% agar. The seeds germinated and were grown at 22° C. in a 16-8 hour light-dark cycle with light intensity approximately 65 µEm$^{-2}$s$^{-1}$. After 5 days the seedlings were taken under sterile conditions and the hypocotyls excised and cut into pieces of about 4 mm in length. The hypocotyl segments were placed on a feeder plate described in Example III or without the feeder layer on top of a filter paper on the solidified B5 0/1/1 medium. This was done 24 hours prior to Agrobacterium treatment.

*Agrobacterium tumefaciens* (strains A281×767 and EHA101×767) were prepared by incubating a single colony of Agrobacterium in MG/L broth at 30° C. Bacteria were harvested 16 hours later and dilutions of $10^8$ bacteria per ml were prepared in MG/L broth. Hypocotyl segments were inoculated with bacteria by placing in Agrobacterium suspension and allowed to sit for 30–60 minutes, then removed and transferred to Petri plates containing B5 0/1/1 medium described above. The plates were incubated in low light at 22° C. The co-incubation of bacteria with the hypocotyl segments took place for 24–48 hours. The hypocotyl segments were removed and placed on B5 0/1/1 containing 500 mg/l carbenicillin (kanamycin sulfate at 10, 25, or 50 mg/l was sometimes added at this time) for 7 days in continuous light (approximately 65 µEm$^{-2}$s$^{-1}$) at 22° C. They were transferred to B5 medium with 3 mg/l BAP and 1 mg/l zeatin as described in Example III. This was supplemented with 500 mg/l carbenicillin, 10, 25, or 50 mg/l kanamycin sulfate, and solidified with 0.6%, Phytagar (Gibco). Thereafter explants were transferred to fresh medium every 2 weeks.

After 1 month green shoots developed from green calli which were selected on media containing kanamycin. Shoots continued to develop for 3 months. The shoots were cut from the calli when they were at least 1 cm high and placed on B5 medium with 1% sucrose, no added growth substances, 300 mg/l carbenicllin, and solidified with 0.6% phytagar. The shoots continued to growth and several leaves were removed to test for neomycin phosphotransfersase II (NPTII) activity. Shoots which were positive for NPTII activity were placed in Magenta boxes containing B5 medium with 1% sucrose, 2 mg/l indolebutyric acid, 200 mg/l carbenicillin, and solidified with 0.6% Phytagar. After a few weeks the shoots developed roots and were transferred to soil. The plants were grown in a growth chamber at 22° C. in a 16-8 hours light-dark cycle with light intensity 220 µEm$^{-2}$s$^{-1}$ and after several weeks were transferred to the greenhouse.

Leaves were harvested, frozen in liquid nitrogen and DNA extracted (Dellaporta et al., *Pl. Molec. Biol. Reporter* (1983) 1:19–21). Southern analysis (Maniatis et al., "Molecular Cloning", Cold Spring Harbor Press) confirmed proper integration of the T-DNA.

Using the method described above 2% of the hypocotyl segments produced shoots which were positive for NPTII activity.

| Frequency of hypocotyl explants producing NPTII positive shoots | | |
|---|---|---|
| Date | Agrobacterium Strain EHA101pCGN767 | A281 pCGN767 |
| 1 | 1/59 2% | 1/59 2% |
| 2 | 1/57 2% | |
| 3 | 1/59 2% | 1/54 2% |

| Frequency of hypocotyl explants producing NPTII positive shoots -continued | | |
|---|---|---|
| Date | Agrobacterium Strain EHA101pCGN767 | A281 pCGN767 |
| | 1/62 2% | 1/60 2% |
| | 1/64 2% | 1/59 2% |
| | 2/58 3% | 1/60 2% |
| | 1/58 2% | 1/59 2% |
| | 2/61 3% | 1/59 2% |

Transgenic plants have been also obtained from hypocotyl segments of *B. napus* cultivars Westar, Viking and Bridger cocultivated with Agrobacterium strains EHA101 and K61 containing other constructs with other plant genes. The system is repeatable with different Agrobacterium strains, constructs, and Brassica genotypes.

EXAMPLE VI

The shoot regeneration frequency from hypocotyl segments was increased at least two-fold by removing kinetin from the cocultivation and callusing medium (B5 0/1/1 to B5 0/1/0).

| Frequency of hypocotyl explants producing at least one shoot | | | | | |
|---|---|---|---|---|---|
| | *B. napus* | Callusing medium | | | |
| Date | cultivar | B5 0/1/0 | | B5 0/1/1 | |
| 1 | Westar | 13/22 | 59% | 3/24 | 12% |
| 2 | Westar | 12/20 | 60% | 2/28 | 7% |
| 3 | Westar | 17/23 | 74% | 3/24 | 12% |
| 4 | Westar | 26/29 | 90% | 12/28 | 43% |
| 5 | Viking | 95/100 | 95% | 53/102 | 52% |
| 6 | Bridger | 58/101 | 57% | 13/77 | 17% |

This change provides an increased number of transformed shoots recovered from hypocotyl explants which were inoculated with Agrobacterium.

The above results demonstrate that Brassica species can be transformed efficiently, whereby foreign genes may be integrated into the plant genome and expressed, providing novel phenotypic properties. Thus, Brassica species can be transformed and are shown to be capable of utilizing genes where the transformed cells may be regenerated into plants which provide for expression of the novel phenotypes. By virtue of the high transformation efficiency, successful transformations can be achieved within reasonable time periods and without unduly repetitive procedures.

All patents, other publications, and patent applications mentioned above are illustrative of the skill of those skilled in the art to which the invention pertains. Each patent, other publication and patent application is herein individually incorporated by reference in the same location and to the same extent as if each patent, other publication, or patent application had been individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. Transgenic Brassica species cells and progeny thereof comprising an expression cassette, wherein said cells are characterized as oncogene-free and capable of regeneration to morphologically normal whole plants, and wherein said expression cassette comprises, in the 5'-3' direction of transcription:

(1) a transcription initiation region functional in Brassica species cells;
(2) a DNA sequence comprising an open reading frame having an initiation codon at its 5' terminus or a nucleic acid sequence complementary to an endogenous transcription product; and
(3) a transcription termination region functional in Brassica species cells;
wherein at least one of said transcription initiation region and transcription termination region is not naturally associated with said DNA sequence or said nucleic acid sequence; and
wherein said expression cassette imparts a detectable trait when said Brassica species cells are grown under conditions whereby said DNA sequence or said nucleic acid sequence is expressed.

2. Cells according to claim 1, wherein said expression cassette is bordered by the right and left T-DNA borders of a Ti- or Ri-plasmid.

3. Cells according to claim 1, wherein said cells further comprise a marker gene for selection of said transgenic Brassica species cells.

4. Cells according to claim 1, wherein said Brassica is *napus* or *campestris*.

5. Cells according to claim 1, wherein said transcription initiation region is from the 35S gene of cauliflower mosaic virus.

6. A cell culture of cells according to claim 1.

7. A cell culture of cells according to claim 3, wherein said culture is capable of growth in a culture medium which includes a selective agent to which said marker gene provides resistance.

8. A method for transforming Brassica species cells to produce morphologically normal whole Brassica plants capable of having an altered phenotype as a result of said transformation, said method comprising:

co-cultivating a Brassica leaf explant with disarmed *A. tumefaciens* comprising a plasmid containing an expression cassette joined to at least a right T-DNA border, whereby said expression cassette becomes integrated into the genome of cells in said Brassica explant to provide transformed oncogene-free cells;
transferring said explant to callus inducing medium comprising approximately 1 mg/l of one or more growth regulators selected from the group consisting of 2,4-D, kinetin and zeatin to allow callus to form on said explant;
transferring said callus to regeneration medium containing less than about 2% sucrose, or an organic caloric equivalent thereto, and comprising at least one milligram per liter of a cytokinin, and a means for selecting for transformed cells as a result of a marker carried on said plasmid, whereby shoots comprising transformed cells are produced from said callus; and
transferring said shoots to a growing medium to produce plants capable of having an altered phenotype when grown under conditions whereby a DNA sequence in said expression cassette is expressed.

9. The method of claim 8 wherein said expression cassette comprises (1) a transcription initiation region functional in Brassica species cells;
(2) a DNA sequence comprising an open reading frame having an initiation codon at its 5' terminus or a nucleic acid sequence complementary to an endogenous transcription product which when expressed will alter the phenotype of said transgenic cells; and
(3) a transcription termination region functional in Brassica species cells.

10. A method according to claim 8, wherein said callus inducing medium further comprises a means for selecting for transformed cells as a result of a marker gene carried on said plasmid.

11. A transformed Brassica plant produced according to the method comprising:

co-cultivating a Brassica leaf or hypocotyl explant with disarmed *A. tumefaciens* comprising a plasmid containing an expression cassette joined to at least a right T-DNA border, whereby said expression cassette becomes integrated into the genome of cells in said Brassica explant to provide transformed oncogene-free cells, and wherein said expression cassette comprises a neomycin phosphotransferase II gene conferring kanamycin resistance;
transferring said explant to callus inducing medium comprising at least one auxin to allow callus to form on said explant;
transferring said callus to regeneration medium containing less than about 2% sucrose, or an organic caloric equivalent thereto, and comprising at least one milligram per liter of a cytokinin, and a means for selecting for transformed cells as a result of expression of said neomycin phosphotransferase II gene, whereby shoots comprising transformed cells are produced from said callus; and
transferring said shoots to a growing medium to produce plants.

12. A plant according to claim 11, wherein said callus inducing medium has about 1 mg/l of an auxin and from about 0 to 1 mg/l of cytokinin, and wherein said regeneration medium contains about 1% sucrose.

13. A method according to claim 8, wherein said Brassica is of the species *campestris* or *napus*.

14. A plant according to claim 11, wherein said callus inducing medium is free of cytokinins.

15. A method according to claim 8, wherein said regeneration medium contains about 1% sucrose.

16. A plant according to claim 11, wherein said Brassica tissue explant is a hypocotyl explant.

17. A plant according to claim 11, wherein said callus inducing medium is free of cytokinins.

18. A plant according to claim 11, wherein said regeneration medium contains about 1% sucrose.

19. A cell culture of stably transformed Brassica species cells, wherein said cells are capable of regeneration into morphologically normal whole Brassica plants capable of having an altered phenotype as a result of said transformation and regeneration, and wherein said cells are produced according to a method comprising:

co-cultivating a Brassica leaf or hypocotyl explant with disarmed *A. tumefaciens* comprising a plasmid containing an expression cassette joined to at least a right T-DNA border, whereby said expression cassette becomes integrated into the genome of cells in said Brassica tissue explant to provide transformed oncogene-free cells;
transferring said tissue explant to callus inducing medium to produce callus comprising stably transformed cells, wherein said callus inducing medium contains at least one auxin and a means for selecting for transformed cells as a result of a marker carried on said plasmid.

20. Transgenic Brassica species cells and progeny thereof comprising an expression cassette, wherein said cells are characterized as oncogene-free and capable of regeneration to morphologically normal whole plants, and wherein said expression cassette comprises, in the 5' to 3' direction of transcription:

(1) a transcription initiation region functional in Brassica species cells;

(2) a DNA sequence comprising a gene of interest encoding a protein product or a nucleic acid sequence complementary to an endogenous transcription product which when expressed will alter the phenotype of said transgenic cells; and (3) a transcription termination region functional in Brassica species cells;

wherein said expression cassette further comprises a structural gene capable of expression in said Brassica species cells and providing for selection of Brassica species cells comprising said structural gene, and a right border region of T-DNA capable of providing for integration of said expression cassette into the genome of said Brassica species cells; and wherein said gene of interest or said nucleic acid sequence is expressed and imparts a detectable trait to said Brassica species cells.

21. Cells according to claim 20, wherein said Brassica species is *napus* or *campestris*.

22. Cells according to claim 20, wherein said transcription initiation region is the 35S region of cauliflower mosaic virus.

23. A cell culture of cells according to claim 20.

24. A cell culture of cells according to claim 23, wherein said culture is capable of growth in a culture medium which includes a selective agent to which said structural gene provides resistance.

25. Cells according to claim 1, wherein said expression cassette is bordered by the right T-DNA border of a Ti- or Ri-plasmid.

26. Cells according to claim 1, wherein said DNA sequence is a neomycin phosphotransferase II gene conferring kanamycin resistance.

27. A Brassica plant comprising cells according to claim 26.

28. A Brassica plant according to claim 27, wherein said Brassica is of the species *campestris* or *napus*.

29. Cells according to claim 3, wherein said marker gene is a neomycin phosphotransferase II gene conferring kanamycin resistance.

* * * * *